US008927236B2

(12) United States Patent
Ashiuchi et al.

(10) Patent No.: US 8,927,236 B2
(45) Date of Patent: Jan. 6, 2015

(54) PROCESS FOR PRODUCING POLY-γ-GLUTAMIC ACID HAVING HIGH OPTICAL PURITY (75) Inventors: Makoto Ashiuchi, Kochi (JP); Kazuki Shimizu, Kochi (JP)

(73) Assignee: Kochi University, Kochi (JP)

( * ) Notice: Subject to any disclaimer, the term of this patent is extended or adjusted under 35 U.S.C. 154(b) by 1646 days.

(21) Appl. No.: 12/223,067

(22) PCT Filed: Jan. 31, 2007

(86) PCT No.: PCT/JP2007/051623
§ 371 (c)(1),
(2), (4) Date: Jul. 22, 2008

(87) PCT Pub. No.: WO2007/088903
PCT Pub. Date: Aug. 9, 2007

(65) Prior Publication Data
US 2010/0233764 A1 Sep. 16, 2010

(30) Foreign Application Priority Data

Feb. 3, 2006 (JP) .................. 2006-027211
Sep. 6, 2006 (JP) .................. 2006-241632

(51) Int. Cl.
*C12P 13/14* (2006.01)
*C12R 1/11* (2006.01)
*C12P 21/02* (2006.01)

(52) U.S. Cl.
CPC . *C12R 1/11* (2013.01); *C12P 13/14* (2013.01); *C12P 21/02* (2013.01)
USPC ........................................ 435/110

(58) Field of Classification Search
None
See application file for complete search history.

(56) References Cited

U.S. PATENT DOCUMENTS

2003/0175936 A1 9/2003 Tahara

FOREIGN PATENT DOCUMENTS

| JP | 08-242880 A | 9/1996 |
| JP | 2000 072652 | 3/2000 |
| JP | 2000 333690 | 12/2000 |

OTHER PUBLICATIONS

Ashiuchi et al., Journal of Molecular Catalysis B: Enzymatic 23 (2003) 249-255.*
Berekaa et al. Journal of Biological Sciences 6 (4): 687-694, 2006.*
M. Ashinai, et al., "'Natto no Ito' no Shuseibun Poly-γ-Glutamate san: sono Kino to Seisan Mechanism", Bioscience to Industiry, 2002, vol. 60, No. 1, pp. 27-30.
M. Ashinai, et al., "Kyodaikin *Bacillus megaterium* o Riyo shita bio Nylon no Koritsu Seisan", The Society for Biotechnology, Japan Taikai Koen Yoshishu, Aug. 3, 2006, vol. 58, p. 63.
M. Ashiuchi, et al., "Novel Poly-γ-Glutamate-Processing Enzyme Catalyzing γ-Glutamyl DD-Amidohydrolysis", Journal of Bioscience and Bioengineering, Jun. 2006, vol. 102, No. 1, pp. 60-65.
M. Ashiuchi, et al., "Isolation of *Bacillus subtilis* (chungkookjang), a poly-γ-glutamate producer with high genetic competence", Appl Microbiol Biotechnol, 2001, vol. 57, pp. 764-769.
Y. Ito, et al., "Glutamic Acid Independent Production of Poly(γ-glutamic acid) by *Bacillus subtilis* TAM-4", Biosci. Biotech. Biochem., 1996, vol. 60, No. 8, pp. 1239-1242.
A.M. Cromwick, et al., "Effects of pH and Aeration on γ-Poly(glutamic acid) Formation by *Bacillus licheniformis* in Controlled Batch Fermentor Cultures", Biotechnology and Bioengineering, 1996, vol. 50, pp. 222-227.
M. Ashiuchi, et al., "Enzymatic Synthesis of High-Molecular-Mass Poly-γ-Glutamate and Regulation of Its Stereochemistry", Applied and Environmental Microbiology, Jul. 2004, vol. 70, No. 7, pp. 4249-4255.
Y. Ogawa, et al., "Efficient Production of γ-Polyglutamic Acid by *Bacillus subtilis* (natto) in Jar Fermenters", Biosci. Biotech. Biochem., 1997, vol. 61, No. 10, pp. 1684-1687.
C. Park, et al., "Synthesis of super-high-molecular-weight poly-γ-glutamic acid by *Bacillus subtilis* subsp. chungkookjang", Journal of Molecular Catalysis B: Enzymatic, 2005, vol. 35, pp. 128-133.
S. Utsumi, "Immunochemical Studies of Bacterial Glutamyl Polypeptides", Biken's Journal, 1959, vol. 2, pp. 165-176.
Ashinai M and Misono H, Function and Production Mechanism of Poly-gamma-glutamate, a Main Component of "Natto Mucilage," Bioscience to Industry, vol. 60, No. 1, Jan. 1, 2001, pp. 27-30 (partial translation attached).
European Search Report dated Aug. 24, 2010, 5 pages.
Office Action in corresponding Japanese Application No. 2006-241632 with English translation, dated Mar. 13, 2012.

* cited by examiner

*Primary Examiner* — Irene Marx
(74) *Attorney, Agent, or Firm* — Bacon & Thomas, PLLC (57) ABSTRACT

It is an objective of the present invention to provide a process for efficiently producing poly-γ-glutamic acid having a high L-glutamic acid content and excellent quality. The process for producing poly-γ-glutamic acid according to the present invention is characterized in using a bacterium belonging to species *Bacillus megaterium*.

10 Claims, 6 Drawing Sheets

PROCESS FOR PRODUCING POLY-γ-GLUTAMIC ACID HAVING HIGH OPTICAL PURITY

TECHNICAL FIELD

The present invention relates to a process for efficiently producing a poly-γ-glutamic acid having high optical purity.

BACKGROUND ART

In recent years, natto has drawn attention by a boom in health care, and studies on natto mucilage have also progressed. The natto mucilage is mainly constituted of poly-γ-glutamic acid produced by *Bacillus subtilis* var. *natto*, i.e. a bacterium belonging to species *Bacillus subtilis* (hereinafter, "*Bacillus*" may be abbreviated as "B." in some cases), and further, various uses of poly-γ-glutamic acid itself have been found out.

For example, Japanese publication of unexamined application No. 2000-72652 discloses the use of poly-γ-glutamic acid as cosmetics based on an excellent water-retaining property thereof. In addition, poly-γ-glutamic acid is also expected for use as environment-friendly new material as well as polylactic acid, since poly-γ-glutamic acid is biodegradable. Further, poly-γ-glutamic acid is highly useful, since poly-γ-glutamic acid is a nonrigid plastic, whereas biodegradable polyester materials such as polylactic acid are fundamentally rigid plastics.

In a process for producing poly-γ-glutamic acid, a bacterium belonging to genus *Bacillus* has been conventionally used. For example, according to Japanese publication of unexamined application No. 2000-333690, it is said that poly-γ-glutamic acid could be more efficiently produced by using a bacterium belonging to genus *Bacillus* capable of producing poly-γ-glutamic acid and having deleted or decreased glutamic acid synthetase activity, compared to a process using normal bacteria belonging to genus *Bacillus*. However, a large amount of antibiotics should be added to a culture medium which is a field for production of poly-γ-glutamic acid and the fear of secondary contamination with recombinant products is not avoidable in the technology.

In the publication of No. 2000-333690, the bacteria to be used is comprehensively described as "the genus *Bacillus*", and *B. licheniformis, B. anthracis* and *B. megaterium* other than *B. subtilis* are disclosed. However, the strains specifically exemplified therein are only strains belonging to species *B. subtilis* known as *Bacillus* natto, and the strain used in Examples is only bacteria belonging to species *B. subtilis*.

In addition, among the bacteria belonging to genus *Bacillus* described in the publication of No. 2000-333690, investigation on productivity of poly-γ-glutamic acid by *B. megaterium* has not been substantially carried out so far, and even superiority or inferiority as a poly-γ-glutamic acid-producing species and characteristics thereof have not yet been known.

The poly-γ-glutamic acid found widely in the natural world tend to be a hybrid polymer including both of D-glutamic acid and L-glutamic acid in many cases. For example, the poly-γ-glutamic acid produced by a bacterium belonging to species *Bacillus subtilis*, which is typically *Bacillus natto*, contains approximately equivalent amounts of L-glutamic acid and D-glutamic acid, or contains D-form in a slightly much more amount (refer to M. Ashiuchi et al., Appl. Microbiol. Biotechnol., vol. 57, pp. 764-769 (2001)).

It is common that the higher the optical purity of a polymer material including a compound having an optical isomer is, the more excellent the characteristics thereof is. For example, the poly-γ-glutamic acid having a high content of L-glutamic acid has higher water-retentivity. Moreover, the poly-γ-glutamic acid having a high content of one optical isomer is extremely excellent as a plastic material, since the crystallinity and intensity of such a material are highly increased.

There is a poly-γ-glutamic acid having high optical purity among poly-γ-glutamic acid obtained from the natural world. For example, *Natrialba aegyptiaca*, which is a kind of halophilic archaea, produces L-glutamic acid-rich poly-γ-glutamic acid in order to protect itself from a dehydration phenomenon which occurs under extreme environment where the salt concentration is extremely high. In general, the poly-γ-glutamic acid having low optical purity produced by a bacterium belonging to species *B. subtilis* rapidly loses water-retentivity, when salts coexist. On the other hand, the poly-γ-glutamic acid having high optical purity derived from halophilic archaea has an extremely excellent water-retaining action. Therefore, it was expected that the poly-γ-glutamic acid having higher quality can be produced by using halophilic archaea.

However, the productivity of halophilic archaea for poly-γ-glutamic acid is far inferior to *Bacillus* natto and the like. In addition, poly-γ-glutamic acid is almost not produced, when halophilic archaea are cultivated in a liquid culture medium which is suitable for mass production. It is practically concluded that halophilic archaea are not suitable for production of poly-γ-glutamic acid having high optical purity.

There are quite a few bacteria which produce poly-γ-glutamic acid regardless of addition or no addition of L-glutamic acid among species *B. subtilis* (refer to Y. Ito, et al., Biosci. Biotechnol. Biochem., vol. 60, pp. 1239-1242 (1996)). In this case, production of poly-γ-glutamic acid is frequently started at the middle stage of culture, and the viscosity of the culture medium is increased in association with the production, resulting in the state where dissolved oxygen is decreased, which is fatal for the growth of aerobic bacteria belonging to species *B. subtilis* (refer to A. M. Cromwick, Biotechnol. Bioeng., vol. 50, pp. 222-227 (1996)). As a result, the bacterial cells cannot be obtained in a sufficient amount, and more efficient production of poly-γ-glutamic acid becomes difficult.

DISCLOSURE OF THE INVENTION

As mentioned above, a bacterium belonging to species *B. subtilis* is known to be used for efficiently producing poly-γ-glutamic acid. However, the poly-γ-glutamic acid produced by the bacterium belonging to species *B. subtilis* has a structure wherein D- and L-glutamic acids are arranged at random, whereas the poly-γ-glutamic acid having a high L-glutamic acid content and higher quality has been demanded for the practical use.

Accordingly, it is the objective to be solved by the present invention is to provide a process for efficiently producing poly-γ-glutamic acid having a high L-glutamic acid content and excellent quality.

The inventors have advanced search of microorganisms suitable for production of poly-γ-glutamic acid having especially high quality in order to solve the problem as mentioned above. As a result, the inventors have found that not the species *B. subtilis* known as *Bacillus natto*, but *B. megaterium* which is a macro bacterium can efficiently produce poly-γ-glutamic acid having high quality, and the present invention has been completed.

The process for producing poly-γ-glutamic acid of the present invention is characterized in using a bacterium belonging to species *Bacillus megaterium*. This process is very useful, since the process can produce poly-γ-glutamic acid having high quality wherein L-glutamic acid content is especially 90% or more.

In the above-mentioned process, it is preferable that the bacterium belonging to species *Bacillus megaterium* is cultivated in a liquid culture medium. This is because the cultivation in the liquid culture medium is suitable for mass production of poly-γ-glutamic acid.

In the above-mentioned method, it is preferable that a production amount and molecular mass of the poly-γ-glutamic acid are adjusted by a sodium chloride concentration in the culture medium.

In the conventional method for the production of poly-γ-glutamic acid by the bacterium belonging to species *B. subtilis*, the concentration of sodium chloride in the culture medium is generally low, and both of the production amount and molecular mass are decreased when the sodium chloride concentration is increased. In contrast, both of the production amount and molecular mass are low when the concentration of sodium chloride in the culture medium is low in the production of poly-γ-glutamic acid by the bacterium belonging to species *B. megaterium*, according to the finding by the inventors. On the other hand, the production amount is increased and poly-γ-glutamic acid having a molecular mass of at least 2000 kDal is obtained, when the sodium chloride concentration is increased. Accordingly, since the growth rate is extremely decreased when bacteria start to produce poly-γ-glutamic acid, the bacterium belonging to species *B. megaterium* is sufficiently precultured in the culture medium having a low concentration and a low content of sodium chloride so that the number of bacteria is increased, and then poly-γ-glutamic acid having a high molecular mass can be efficiently produced in the culture medium having a high sodium chloride concentration.

In the above-mentioned process, it is preferable that the production amount of the poly-γ-glutamic acid is adjusted by addition or no addition of L-glutamic acid to the culture medium. Specifically, it is observed that, in the case where poly-γ-glutamic acid is produced by bacteria, the production of poly-γ-glutamic acid starts at the middle stage of the culture, and not only the production amount is decreased, but also bacteria do not grow, after poly-γ-glutamic acid is produced in a sufficient amount for bacteria. Therefore, it is ideal for efficient production of poly-γ-glutamic acid that bacteria fully grow at first without producing poly-γ-glutamic acid, and then the production is made to start. According to the finding by the inventors, the production amount of poly-γ-glutamic acid is remarkably suppressed when there is no L-glutamic acid in the culture medium. Therefore, it is possible to adjust the production amount of poly-γ-glutamic acid and the growth of bacteria by addition or no addition of L-glutamic acid.

It is preferable that $Mg^{2+}$ is used as a polyvalent metal ion in the culture medium or the culture medium not substantially containing $Mn^{2+}$ is used. According to the finding by the inventors, the content of D-glutamic acid in poly-γ-glutamic acid is increased when $Mn^{2+}$ is present in the culture medium. On the other hand, $Mg^{2+}$ is useful for increasing the content of L-glutamic acid. Therefore, the above embodiments are effective in enabling to efficiently produce L-glutamic acid-rich poly-γ-glutamic acid.

BEST MODE FOR CARRYING OUT THE INVENTION

The process for producing poly-γ-glutamic acid (PGA) of the present invention is characterized in using a bacterium belonging to species *Bacillus megaterium*. More specifically, the process includes culturing the bacterium belonging to species *B. megaterium* in a culture medium and recovering poly-γ-glutamic acid released outside the cell.

The bacterium belonging to species *B. megaterium* used in the process of the present invention is a rod-shaped huge Gram-strain positive *bacillus* having a size of about 2 to 6 μm×1.5 μm. According to the finding by the inventors, when PGA is produced by using the bacterium belonging to species *B. megaterium*, PGA having a high content of L-glutamic acid (hereinafter, referred to as "L-Glu" in some cases) and high quality can be obtained depending on the culture conditions.

The bacterium belonging to species *B. megaterium* which can be used is not particularly limited so long as the bacterium has a productivity of PGA, and, for example, a WH320 strain is exemplified as a useful microorganism.

It is preferable to sufficiently preculture the bacterium belonging to species *B. megaterium* before PGA production. The culture conditions may be appropriately adjusted depending on the bacterium belonging to species *B. megaterium* to be used. For example, the bacterium is cultured in a normal LB medium containing polypeptone, yeast extract and sodium chloride at 30 to 45° C. for about 12 hours to 2 days. It is preferable not to substantially add L-Glu to the preculture medium. The term, "not to substantially add", means that L-Glu is not further added except for L-Glu contained in yeast extract and the like. In case that L-Glu is sufficiently present in the culture medium, the bacterium belonging to species *B. megaterium* may start to produce PGA, leading to a fear that the growth of bacterium may be suppressed.

After the preculture, the bacterial cells are separated by centrifugation or the like, further washed with a physiological saline solution several times to be used for PGA production.

In the present invention, PGA is produced by culturing the bacterium belonging to species *B. megaterium* under suitable conditions. By employing suitable conditions, PGA having a high L-Glu content, more specifically an L-Glu content of 90% or more, and having high quality can be obtained.

The ratio of L-Glu can be measured, for example, by the following method. First, PGA as measurement object is collected, dissolved in 6N hydrochloric acid, and subjected to hydrolysis reaction at 105° C. for about 8 hours. On this occasion, since the main structure of PGA is a so-called polyisopeptide via not an α-amide bond but a γ-amide bond, racemization hardly occur. The glutamic acid contained in the obtained hydrolysate is analyzed by a chiral resolving HPLC (refer to M. Ashiuchi et al., Appl. Environ. Microbiol., vol. 70, p. 4249 to 4255 (2004)), and the content ratio of D-form and L-form is determined to calculate the L-Glu content.

There are a solid culture medium and a liquid culture medium as a culture medium. Among them, the liquid culture medium is more suitable in the present invention. By the solid culture medium, it is difficult to make PGA produce sufficiently, and recovery of PGA is also troublesome. On the other hand, the liquid culture medium is suitable for mass production, and the recovery of PGA is also easy by the liquid culture medium.

The additives of the culture medium may be appropriately adjusted. It is preferable to add L-Glu, ammonium sulfate, $Mg^{2+}$ and sodium chloride.

Sodium chloride is an important component for the culture medium in the process of the present invention. The production amount and molecular mass of PGA can be controlled by adjusting the concentration of sodium chloride in the culture medium, in the production of PGA by the bacterium belonging to species *B. megaterium*.

Specifically, in the conventional production method for PGA by a bacterium belonging to species *B. subtilis*, the sodium chloride concentration in a liquid culture medium is generally around 0.05% by mass, and both of the production amount and molecular mass are decreased when the sodium chloride concentration exceeds 3% by mass, (refer to M. Ashiuchi et al., Appl. Microbiol. Biotechnol., vol. 57, p. 764 to 769 (2001); and Y. Ogawa et al., Biosci. Biotechnol. Biochem., vol. 61, p. 1684 to 1687 (1997)). However, according to the finding by the inventors, when the sodium chloride concentration in the culture medium is decreased in a similar manner to the case of the bacterium belonging to species *B. subtilis*, the production amount became to be almost none in the production of PGA by the bacterium belonging to species *B. megaterium*. On the other hand, when the sodium chloride concentration is increased to 2% by mass or more, the production amount is improved. Furthermore, when the sodium chloride concentration is 10% by mass, PGA having a molecular mass of at least 2000 kDal is obtained. Therefore, the bacterium belonging to species *B. megaterium* is first precultured in the culture medium having a low sodium chloride concentration of 0.05% by mass or less to increase the number of the bacteria; and then PGA having a high molecular mass can be efficiently produced in the culture medium containing sodium chloride with a high concentration of 1.5% by mass or more, preferably 2% by mass or more, more preferably 10% by mass or less, most preferably 4% by mass or more and 6% by mass or less; since the growth rate is extremely decreased when bacteria start to produce PGA. Furthermore, such a medium also has an effect of preventing contamination associated with the growth of miscellaneous microorganisms, compared to the conventional method using the bacterium belonging to species *B. subtilis* such as *Bacillus natto*, since the growth of contaminated microorganisms can be suppressed in the culture medium which abundantly contains sodium chloride.

L-Glu is a component required for efficient PGA production. If L-Glu is not present enough in the culture medium, PGA production does not proceed easily. Therefore, it is preferable that the bacterium belonging to species *B. megaterium* is fully proliferated without addition of L-Glu at the initial stage of the culture, and then L-Glu may be added at the time of starting PGA production. The amount of L-glutamic acid to be added may be appropriately adjusted, and it is preferably about 1% by mass or more and about 5% by mass or less, and more preferably about 1% by mass or more and about 3% by mass or less.

Ammonium sulfate is suitable as a nitrogen source, and in particular, combination use of ammonium sulfate with L-Glu enables to efficiently produce PGA. The additional amount may be appropriately adjusted, and the amount is preferably about 0.1% by mass or more and about 3% by mass or less, and more preferably about 0.5% by mass or more and about 2% by mass or less.

As the polyvalent metal ion to be added in the culture medium, $Mg^{2+}$ is suitable. Moreover, it is preferable not to substantially add $Mn^{2+}$ to the culture medium. In the conventional production of PGA by *Bacillus natto* which is bacteria of species *B. subtilis*, $Mn^{2+}$ is mainly used as the polyvalent metal ion. However, according to the finding by the inventors, the L-Glu content in the produced PGA is reduced, when $Mn^{2+}$ is present in the culture medium for the bacterium belonging to species *B. megaterium*. For example, the presence of $Mn^{2+}$ of only 0.05% by mass relative to $Mg^{2+}$ of 0.5% by mass makes the D-Glu content exceed the L-Glu content, according to Examples described below. On the other hand, the L-Glu content is increased, when $Mg^{2+}$ is fully present in the culture medium.

The term, "not to substantially add $Mn^{2+}$", means that any $Mn^{2+}$-containing components are not intentionally added to the culture medium, except for $Mn^{2+}$ which is inevitably contaminated.

It is preferable that $Mg^{2+}$ is added in the form of a water-soluble salt, such as a sulfate salt and a chloride salt. The amount of $Mg^{2+}$ to be added may be appropriately adjusted, and the amount is preferably about 0.05% by mass or more and about 2% by mass or less, and more preferably about 0.1% by mass or more and about 1% by mass or less, in terms of, for example, magnesium sulfate.

In addition to the above additives, any conventional components may be added to the culture medium. Examples of the additives conventionally used include, for example, carbon sources, such as glucose and sucrose; buffer components, such as $Na_2HPO_4$, $K_2HPO_4$, $NaH_2PO_4$ and $KH_2PO_4$; and vitamins.

In the case of the liquid culture medium, usual sterilization may be performed after the above additive components are dissolved in distilled water. In the case of the solid culture medium, about 1 to 2% by mass of agar is further dissolved, and the solution is sterilized and then solidified upon cooling.

The production of PGA may be started by inoculating the bacterium belonging to species *B. megaterium* which has been precultivated into the culture medium containing a proper amount of sodium chloride and L-Glu. Alternatively, the bacterium belonging to species *B. megaterium* is fully cultured in the culture medium not initially containing sodium chloride and L-Glu or in the culture medium containing sodium chloride and L-Glu in a small amount; and then PGA production may be started by addition of sodium chloride and L-Glu; as mentioned above.

As the specific culture conditions, can be adopted the optimum conditions or the conditions close to the optimum conditions for the bacterium belonging to species *B. megaterium* to be used. For example, shaking culture or stationary culture may be carried out at room temperature to 40° C.

The time for the culture is not particularly limited. The culture may be continued until sufficient production of PGA can be confirmed by viewing or the viscosity of the cultured product, and the time may be, for example, about 2 to 10 days.

The obtained poly-γ-glutamic acid may be purified in an ordinary manner. For example, the bacterial cells are removed by centrifugation or filtration; the resulting crude solution is acidified with 6M sulfuric acid to decompose polysaccharides and the like; and an excess amount of ethanol is added thereto to precipitate a high molecular substance containing PGA. Moreover, treatment for degrading the other proteins with proteinase K or the like which does not affect PGA may be timely performed. The resulting precipitates are dissolved in 0.1 M Tris-HCl buffer solution (pH 8.0) or the like, and the solution is repeatedly dialyzed for purification and freeze-dried to obtain PGA. Anion exchange chromatography can be applied when further purification of the polymer is required (refer to C. Park et al., J. Mol. Catal. B: Enzym., vol. 35, p. 128 to 133 (2005)).

The poly-γ-glutamic acid produced by the present invention process has a high content of L-glutamic acid. Therefore, the poly-γ-glutamic acid according to the present invention is excellent in water retentivity and has high intensity, and is very effective as cosmetic components or biodegradable plastic materials, unlike those wherein D-glutamic acid and L-glutamic acid are arranged at random.

EXAMPLES

The present invention is more specifically described by the examples below. It should be understood that the scope of the present invention is not restricted by the examples described below in any way, and any appropriate modifications can be made without departing the gist of the invention described above or below, and such modifications all fall within the scope of the invention.

Example 1

Production Experiment of Poly-γ-Glutamic Acid Using *B. megaterium*: Investigation on Culture Method A WH320 strain of *B. megaterium* (provided by MoBiTec Gmbh, Germany, Gottingen) was sufficiently precultivated in an LB medium (5 mL), which is a liquid culture medium. Moreover, 1 mL of the culture solution was collected and the strain was cultured overnight in a 1 L-flask containing an LB medium (200 mL). The culture medium was washed one or two times with an appropriate amount of a physiological saline solution, and finally suspended into about 2 mL of a physiological saline solution. An aliquot (500 µL) of the suspension was inoculated into an LSN liquid culture medium (50 mL) having the composition as shown in Table 1 below, and the strain was cultured at 30° C. for 5 days to produce PGA. The percentage in Table 1 is expressed in terms of % by mass, and Murashige and Skoog Vitamin Solution (ten-fold concentrated solution) is manufactured by Photo Technology Laboratories (U.S.A.).

TABLE 1

| | |
|---|---|
| Sucrose | 5% |
| L-Glutamic acid | 2% |
| Ammonium sulfate | 1% |
| $KH_2PO_4$ | 0.27% |
| $Na_2HPO_4$ | 0.42% |
| NaCl | 5% |
| $MgSO_4 \cdot 7H_2O$ | 0.5% |
| Murashige and Skoog Vitamin Solution | 10% |

After that, 10 mL of the culture solution was collected to confirm PGA production. Specifically, 6M sulfuric acid was firstly added dropwise to the collected culture solution so that the pH was set to 3.0 in order to decompose a polysaccharide, and then the mixture was left to stand at 4° C. for 12 hours. Next, a 3-fold amount of ethanol was added to the treated solution, and the remaining high molecular substance which was mainly PGA was precipitated and recovered by centrifugation. The resulting precipitate was dissolved in 0.1 M Tris-HCl buffer solution (pH 8.0) and dialyzed at 4° C. all day and night using a 1000-fold amount of the buffer solution. The high molecular substance solution after dialysis was recovered by centrifugation, and proteinase K (manufactured by Takara Shuzo Co. Ltd., 20 µg/mL) was added thereto so that proteins copresent therein were completely dissolved. PGA is completely resistant to this treatment. PGA was further purified by dialysis at 4° C. all day and night by a 1000-fold amount of distilled water. The solution after dialysis was dried by freeze-drying, and finally dissolved in distilled water of 300 µL.

For comparison, agar (1.5%) was added to the LSN liquid culture medium, and the mixture was solidified in a large plate of 145 mm in diameter to make a solid culture medium. The strain was inoculated to the solid medium to produce PGA in a similar manner. The cells which had proliferated on the surface of the solid culture medium were then completely suspended and recovered by using a physiological saline solution (50 mL), and the supernatant containing the polymer was prepared by centrifugation. PGA was purified from the resulting supernatant (10 mL) in a similar manner.

Figure 1:
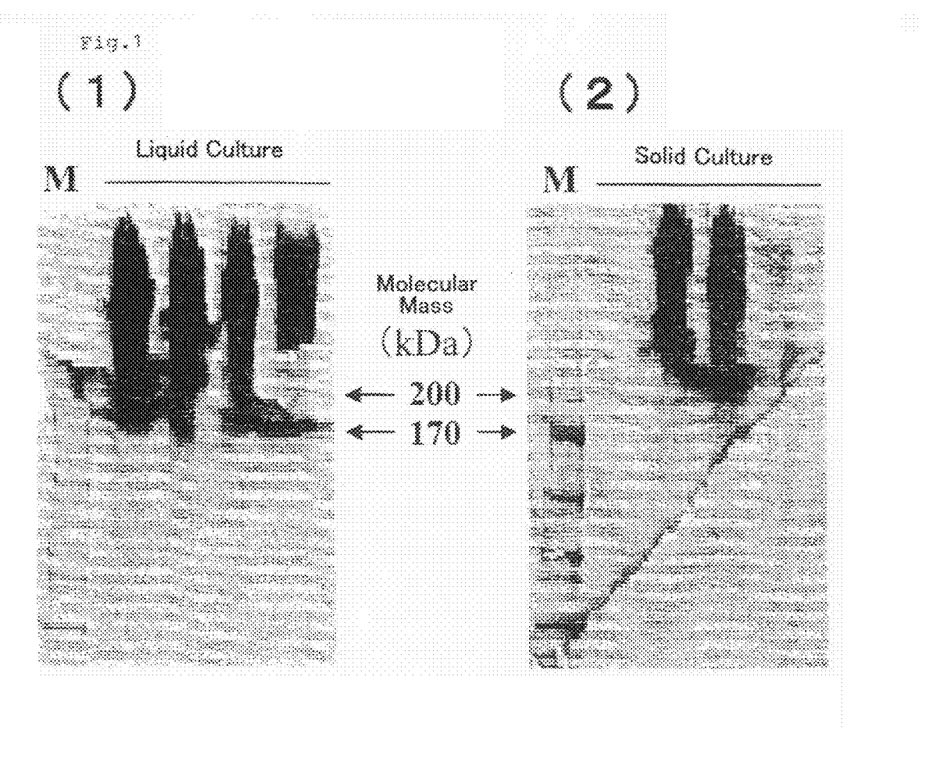
FIG. 1 indicate the results of SDS-PAGE of poly-γ-glutamic acid (hereinafter, referred to as "PGA" in some cases) produced by using *B. megaterium*. In the figure, (1) is a result when a liquid culture medium is used, and (2) is a result when a solid culture medium is used.

Aliquot (10 µL) from the purified solution of every four samples each of PGA obtained above were collected and subjected to SDS-PAGE, and visualization was carried out by methylene blue staining method. The results are shown in FIG. 1. In FIG. 1, (1) shows the result of using the liquid culture medium, and (2) shows the result of using the solid culture medium. In each result, the lane M is the result of electrophoresis of the molecular weight marker (manufactured by Amersham Pharmacia Biotech, England, Little Chalfont).

As shown in FIG. 1, a broad band is observed. This indicates that the produced PGA has various molecular weights.

The PGA has a molecular weight exceeding at least 200 kDa. Moreover, it was elucidated that the reproducibility in the case of cultivating in the liquid culture medium is good and thus PGA could be stably produced, while reproducibility was bad in the case of using the solid culture.

Test Example 1

Ratio of D-Form and L-Form Constituting the Poly-γ-Glutamic Acid

The ratio of D-form and L-form of Glu constituting the PGA was determined by the following method. To an aqueous solution (20 μL) of the PGA obtained in the above Example 1, 6N hydrochloric acid (400 μL) was added, and the mixture was hydrolyzed under heating at 105° C. for 8 hours. In the reaction, since the main structure of PGA was a so-called polyisopeptide via not α-amide bond but γ-amide bond, the racemization hardly occurred. The glutamic acid contained in the obtained hydrolysate was resolved with an HPLC equipment (manufactured by Shimadzu Corp.) provided with a chiral resolving HPLC (manufactured by Dicel Chemical Industries Ltd, 4.6 mm×50 mm), to determine the ratio of D-form and L-form by the peak intensity. In addition, the weight of the bacterial cells used for the PGA production was measured as wet weight using an electronic balance. The production amount of poly-γ-glutamic acid per bacterial cell weight and the ratio of D-Glu and L-Glu in the obtained PGA are shown in Table 2. Each data of Table 2 is an average and a standard error of six experimental results.

TABLE 2

| Culture conditions | Productivity (g/g bacterial cell weight) | Content (%) D-Glu | L-Glu |
|---|---|---|---|
| Solid culture | 0.91 ± 0.74 | 9.8 ± 3.1 | 90.2 ± 3.1 |
| Liquid culture | 2.18 ± 0.28 | 7.6 ± 3.2 | 92.4 ± 3.2 |

As shown in the results of Table 2, it was demonstrated that the PGA produced by *B. megaterium* was constituted of L-Glu exceeding 90%. In addition, it was found that PGA was obtained in a 2-fold amount or more when PGA was produced by the liquid culture medium, compared to the solid culture.

Example 2

Figure 2:
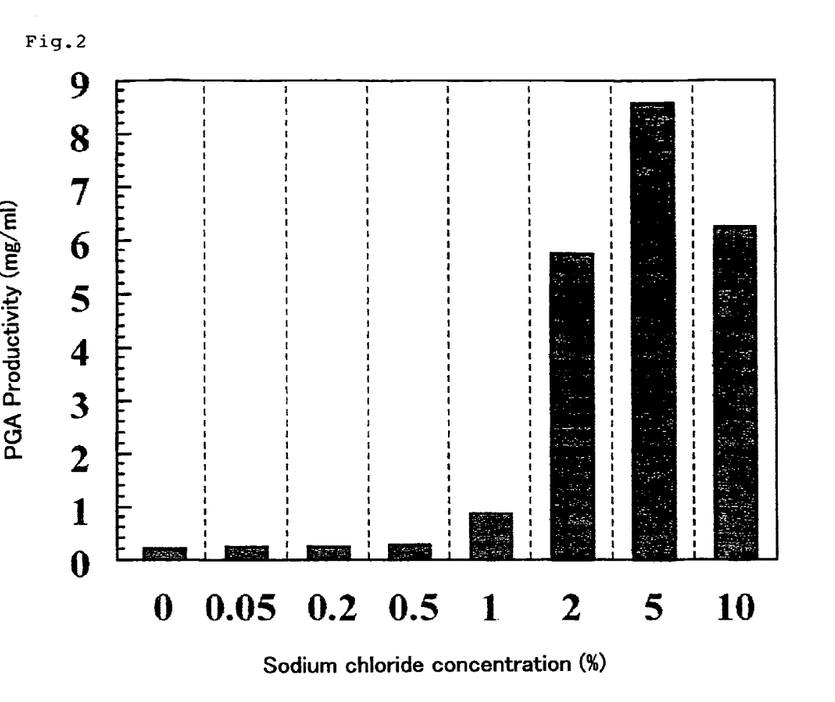
FIG. 2 indicates the result of effect by sodium chloride exerted on PGA production by *B. megaterium*. The vertical axis shows the total amount of PGA per mL of the culture solution, and the horizontal axis shows the concentration of sodium chloride in a modified LSN culture medium.
Figure 3:
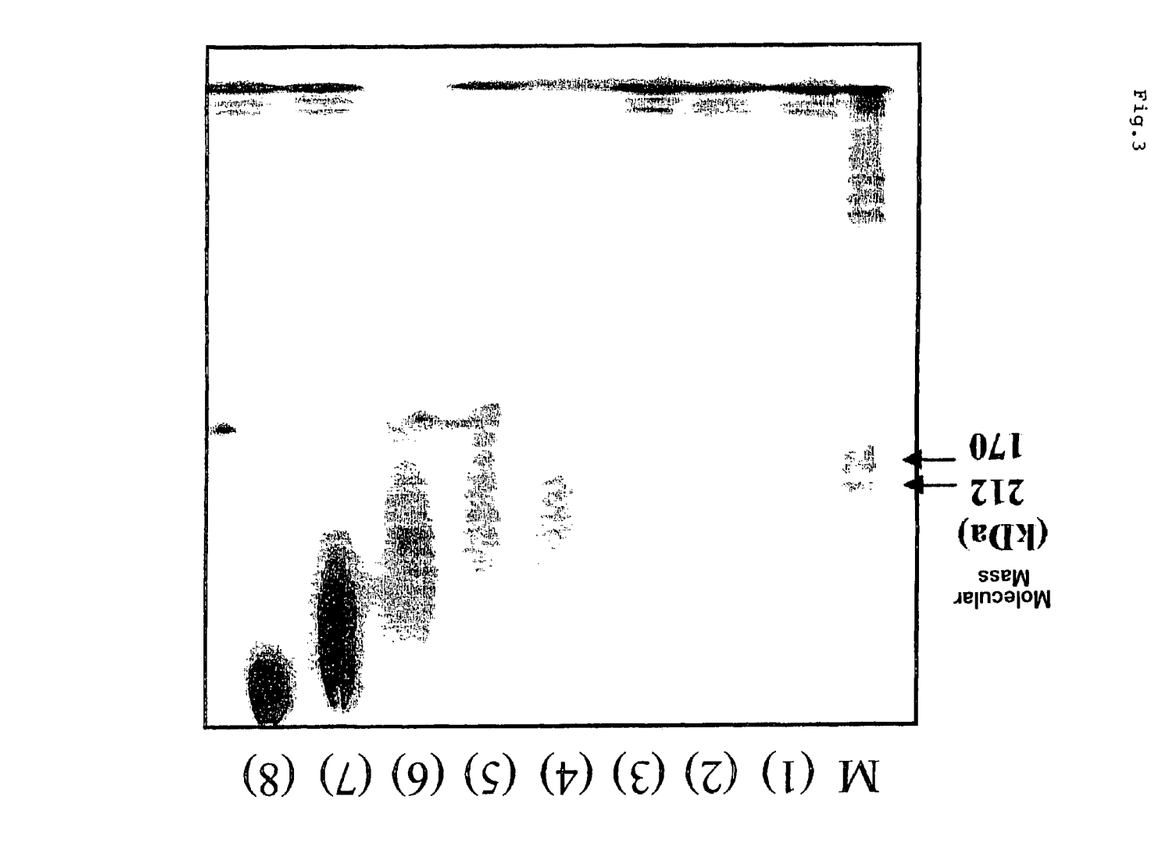
FIG. 3 indicates the results of SDS-PAGE illustrating the additional effect of sodium chloride in the production of PGA using *B. megaterium*. In the figure, (1) is the case of no addition of sodium chloride, (2) is the case of addition of 0.05% by mass, (3) is the case of addition of 0.2% by mass, (4) is the case of addition of 0.5% by mass, (5) is the case of addition of 1% by mass, (6) is the case of addition of 2% by mass, (7) is the case of addition of 5% by mass, and (8) is the case of addition of 10% by mass.

Production Experiment of Poly-γ-Glutamic Acid Using *B. megaterium*: Addition Effect of Sodium Chloride In the LSN liquid culture medium used for the polymer production in the above Example 1, 5% by mass of sodium chloride was contained. Modified culture media with the varied sodium chloride concentrations of 0, 0.05, 0.2, 0.5, 1, 2, 5 and 10% by mass were prepared, and how influences will affect the production of PGA by the sodium chloride concentration was invested. Specifically, *B. megaterium* was cultivated in liquid culture medium to produce PGA under a similar condition to Example 1 except that the LSN liquid culture medium was modified as the above. The experiment by each modified culture medium was carried out twice respectively, and PGA was purified in a similar manner to Example 1 and weighed to calculate the production amount of PGA per mL of the culture solution. The results are shown in FIG. 2. In addition, the resulting PGA solution was subjected to SDS-PAGE and stained with methylene blue in a similar manner to Example 1. The results are shown in FIG. 3.

As shown in the results of FIG. 2, it was proved that PGA can be efficiently produced in a culture medium with a high salt concentration exceeding 2%, and preferably with a concentration of 5%. Accordingly, it was elucidated that production control by sodium chloride concentration is possible in the PGA production using *B. megaterium*. Furthermore, as apparent from the results shown in Table 3, it was clarified that controlling of molecular mass is possible by changing sodium chloride concentration. Special attention should be paid to successful production of PGA having a super-high molecular mass exceeding the measurement limit, i.e. at least 2000 kDal or more, in the case where sodium chloride of 10% was added.

Example 3

Figure 4:
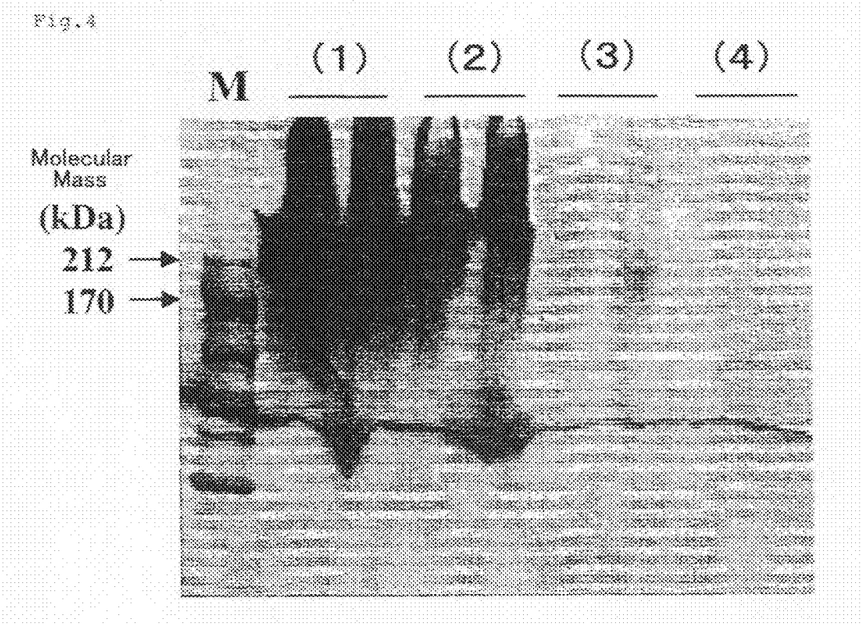
FIG. 4 indicates the results of SDS-PAGE illustrating the influence of a nitrogen source in the production of PGA using *B. megaterium*. In the figure, (1) is the case where L-Glu and ammonium sulfate are used in combination as a nitrogen source, (2) is the case where only L-Glu is used, (3) is the case where only ammonium sulfate is used, and (4) is the case where both are not added.

Production Experiment of Poly-γ-Glutamic Acid Using *B. megaterium*: Investigation on Nitrogen Sources As the above Example 1, (1) 2% L-Glu and 1% ammonium sulfate, i.e. (NH$_4$)$_2$SO$_4$, were standardly used as a nitrogen source in the LSN liquid culture medium used for the production of poly-γ-glutamic acid. On the other hand, modified culture media comprising (2) 2% L-Glu only, (3) 1% ammonium sulfate only and (4) no addition of both were prepared, and how the change of the nitrogen source would affect the PGA production was investigated. Specifically, *B. megaterium* was cultured in liquid culture medium to produce PGA under a similar condition to Example 1 except that the LSN liquid culture medium was modified as the above. The resulting PGA solution was subjected to SDS-PAGE and stained with methylene blue in a similar manner to Example 1. The experiment by each modified culture medium was carried out twice. The results are shown in FIG. 4.

Moreover, the experiment by each modified culture medium was respectively carried out 4 times, and the average of the production amount of PGA per mL of the culture solution and the ratio of D-form and L-form of glutamic acid, calculated by a similar method to the above Test Example 1, are shown in Table 3.

TABLE 3

| Culture conditions | Productivity (mg/mL) | Content (%) D-Glu | L-Glu |
|---|---|---|---|
| L-Glu + (NH$_4$)$_2$SO$_4$ | 8.9 | 8.8 | 91.2 |
| L-Glu | 3.4 | 11.6 | 88.4 |
| (NH$_4$)$_2$SO$_4$ | 0.9 | 23.3 | 76.7 |
| None | 0 | — | — |

As shown in the results of FIG. 4 and Table 3, it is understood that a good result can be significantly obtained by the addition of L-Glu in PGA production with use of *B. megaterium*. This result suggests that PGA production can be controlled by adjusting the time of L-Glu addition. Moreover, it was cleared that the productivity of PGA and the ratio of L-Glu which constitutes PGA are increased by combination use of L-Glu and ammonium sulfate.

Example 4

Figure 5:
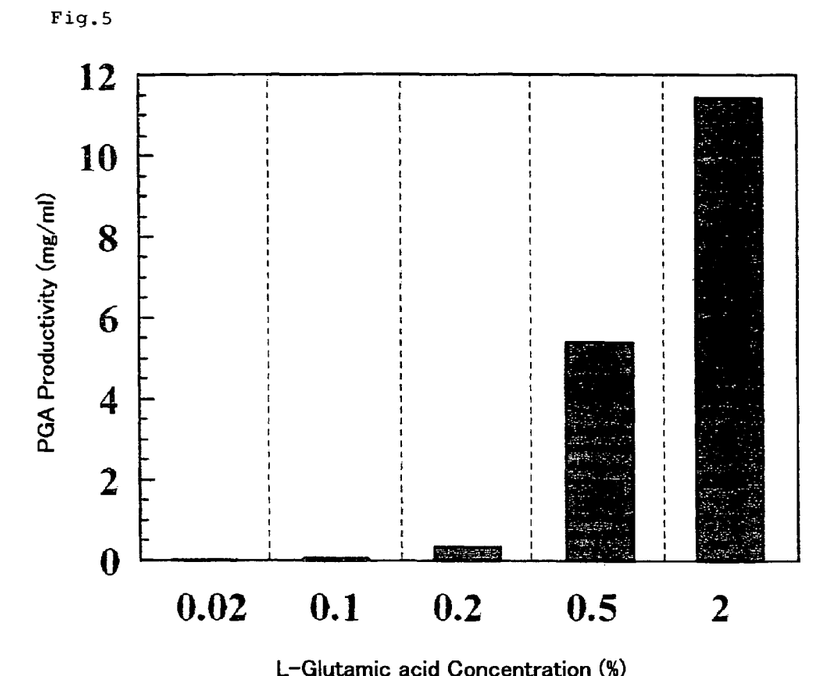
FIG. 5 indicates the results of influence of the L-Glu concentration in the culture medium in the production of PGA using *B. megaterium*. The vertical axis shows the total amount of PGA per mL of the culture solution, and the horizontal axis shows the L-Glu concentration in a modified LSN culture medium.

Production Experiment of Poly-γ-Glutamic Acid Using *B. megaterium*: Effect of L-Glu Concentration Modified culture media wherein the concentration of L-Glu contained in the LSN liquid culture medium of the above Example 1 was changed to 0.02, 0.1, 0.2, 0.5 and 2% by mass were prepared, and how the differences of L-Glu concentration would affect PGA production was investigated. Specifically, *B. megaterium* was cultured in the liquid culture medium to produce PGA under a similar condition to Example 1 except that the LSN liquid culture medium was modified as the above. The experiment by each modified culture medium was carried out two times respectively, and PGA was purified in a similar manner to Example 1 and weighed to calculate the production amount of PGA per mL of the culture solution. The results are shown in FIG. 5. Moreover, the resulting PGA solution was subjected to SDS-PAGE and stained with methylene blue in a similar manner to Example 1. The results are shown in FIG. 6.

Figure 6:
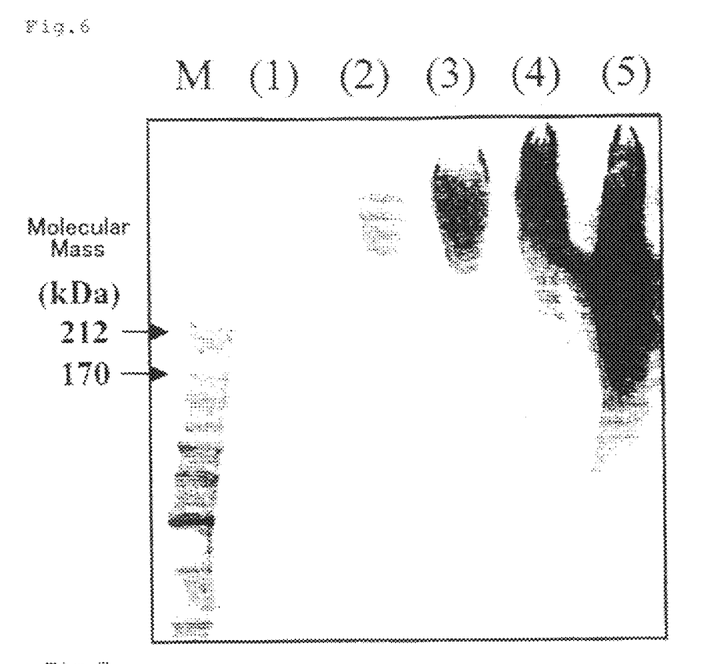
FIG. 6 indicates the results of effect of the L-Glu concentration exerted in the production of PGA using *B. megaterium*. In the figure, (1) is the case where 0.02% by mass of L-Glu is added, (2) is the case where 0.1% by mass is added, (3) is the case where 0.2% by mass is added, (4) is the case where 0.5% by mass is added, and (5) is the case where 2% by mass is added.

As shown in the results of FIG. 5 and FIG. 6, it was cleared that the production amount of PGA by *B. megaterium* was greatly influenced by L-Glu concentration. It was demonstrated that PGA can be efficiently produced in the culture medium containing L-Glu exceeding 0.5%, and 2% is preferable. Although data are not shown, it was confirmed that there is no significant change in the yield, even if L-Glu is added at a high concentration of 2% or more, such as 5%.

Example 5

Production Experiment of Poly-γ-Glutamic Acid Using *B. megaterium*: Influence of Metal Ions Only $Mg^{2+}$ was used as a metal ion which was a production-promoting factor in the LSN liquid culture medium used for the polymer production as shown in the above Example 1. To the contrary, it was investigated how the PGA production would be affected in the case where $Mn^{2+}$ which is frequently used for PGA production of *Bacillus* natto was substituted or coexisted. Specifically, PGA was produced by *B. megaterium* in a similar manner to Example 1, except that the LSN liquid culture media containing (1) 0.5% $MgSO_4.7H_2O$+0.05% $MnCl_2$, (2) only 0.5% $MgSO_4.7H_2O$, (3) only 0.05% $MnCl_2$ and (4) no addition of both were used as a polyvalent metal ion source.

Figure 7:
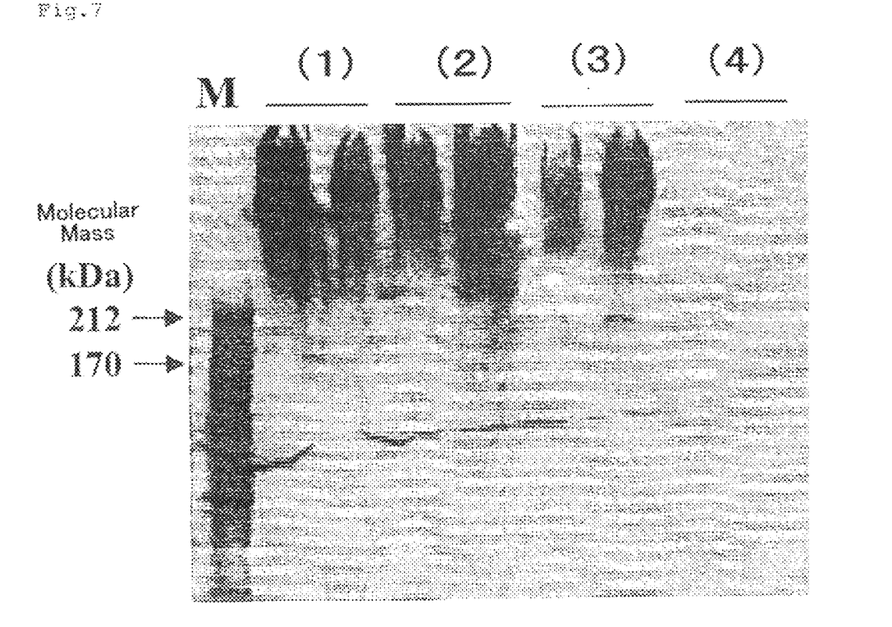
FIG. 7 indicates the results of SDS-PAGE illustrating the influence of polyvalent metal ions in the production of PGA using *B. megaterium*. In the figure, (1) is the case where $Mg^{2+}$ and $Mn^{2+}$ are used in combination as a polyvalent metal ion, (2) is the case where only $Mg^{2+}$ is used, (3) is the case where only $Mn^{2+}$ is used, and (4) is the case where both are not added.

FIG. 7 shows the produced PGA of two independent trials visualized by methylene blue staining method, and Table 4 shows the production amounts and the average values of L-Glu and D-Glu contents of four independent trials.

TABLE 4

| Culture conditions | Productivity (mg/mL) | Content (%) D-Glu | L-Glu |
|---|---|---|---|
| $Mg^{2+}$ + $Mn^{2+}$ | 11.1 | 55.6 | 44.4 |
| $Mg^{2+}$ only | 8.9 | 9.1 | 90.9 |
| $Mn^{2+}$ only | 3.3 | 52.7 | 47.3 |
| None | 0 | — | — |

As shown in the results of Table 4, even if $Mg^{2+}$ is added to the culture medium, the L-Glu content in PGA is decreased to less than 50% just by adding only $Mn^{2+}$ of about 10% of $Mg^{2+}$. On the other hand, it was demonstrated that the L-Glu content in PGA is raised to 90% or more by using only $Mg^{2+}$ as a polyvalent metal ion in the culture medium.

Industrial Applicability

According to the process for producing poly-γ-glutamic acid of the present invention, poly-γ-glutamic acid having high quality and a high L-glutamic acid content can be efficiently produced. Therefore, the present invention is industrially very useful because it becomes possible by the present invention to efficiently produce poly-γ-glutamic acid having high optical purity which can be expected, for example, for use in cosmetic ingredients due to excellent water-retentivity and in biodegradable soft plastic materials.

The invention claimed is:

1. A process for producing poly-γ-glutamic acid, comprising:
   (a) preculturing *Bacillus megaterium* WH320 in a first culture medium having a sodium chloride concentration of 0.05% by mass or less;
   (b) cultivating the *Bacillus megaterium* WH320 in a second culture medium having a high sodium chloride concentration of 1.5% by mass or more; and
   (c) recovering from the second culture medium the poly-γ-glutamic acid released by the *Bacillus megaterium* WH320, wherein the poly-γ-glutamic acid comprises 90% or more L-glutamic acid.

2. The process according to claim 1, wherein the culture medium of step (b) is a liquid culture medium.

3. The process according to claim 1, wherein the amount and molecular mass of the poly-γ-glutamic acid released by the *Bacillus megaterium* WH320 are adjusted by adjusting the sodium chloride concentration in the culture medium of step (b).

4. The process according to claim 1, wherein the amount of the poly-γ-glutamic acid released by the *Bacillus megaterium* WH320 is adjusted by adjusting the L-glutamic acid concentration in the culture medium of step (b).

5. The process according to claim 1, wherein the culture medium of step (b) comprises the polyvalent metal ion $Mg^{2+}$.

6. The process according to claim 1, wherein the culture medium of step (b) does not comprise a substantial amount of $Mn^{2+}$.

7. The process of claim 1, wherein the culture medium of step (b) comprises from 1.5 to 10% sodium chloride by mass.

8. The process of claim 1, wherein the culture medium of step (b) comprises from 0.05 to 2% $Mg^{2+}$ by mass.

9. The process of claim 1, wherein the culture medium of step (b) comprises from 1 to 5% L-glutamic acid by mass.

10. The process of claim 1, wherein the culture medium of step (b) comprises from 0.1 to 3% ammonium sulfate by mass.

* * * * *